US006790410B2

(12) United States Patent
Metzner et al.

(10) Patent No.: US 6,790,410 B2
(45) Date of Patent: Sep. 14, 2004

(54) USE OF A HYDROGEN PEROXIDE PLASMA STERILIZATION METHOD FOR THE MILD STERILIZATION OF TEMPERATURE-SENSITIVE PRODUCTS

(75) Inventors: Hubert Metzner, Marburg (DE); Joerg Lemmer, Ebsdorfergrund (DE); Horst Naumann, Marburg (DE)

(73) Assignee: Aventis Behring GmbH, Marburg (GE)

( * ) Notice: Subject to any disclaimer, the term of this patent is extended or adjusted under 35 U.S.C. 154(b) by 104 days.

(21) Appl. No.: 10/052,469

(22) Filed: Jan. 23, 2002

(65) Prior Publication Data

US 2003/0003014 A1 Jan. 2, 2003

(30) Foreign Application Priority Data

Jan. 26, 2001 (DE) .......................................... 101 03 706

(51) Int. Cl.[7] .............................. A61L 2/14; A61L 2/16
(52) U.S. Cl. .............................. 422/22; 422/23; 422/28; 422/33; 422/186.23
(58) Field of Search .............................. 422/22, 23, 28, 422/33, 186.23, 29, 20, 127, 128

(56) References Cited

U.S. PATENT DOCUMENTS

| | | | |
|---|---|---|---|
| 4,643,876 A | | 2/1987 | Jacobs et al. ................. 422/23 |
| 6,159,422 A | | 12/2000 | Graves et al. ................ 422/23 |
| 6,355,448 B1 | * | 3/2002 | Foltz et al. ................... 435/31 |
| 6,365,102 B1 | * | 4/2002 | Wu et al. ...................... 422/23 |
| 6,458,321 B1 | * | 10/2002 | Platt et al. .................... 422/23 |
| 6,627,150 B1 | * | 9/2003 | Wang et al. .................. 422/33 |

FOREIGN PATENT DOCUMENTS

| | | |
|---|---|---|
| EP | 0 207 417 A1 | 6/1986 |
| EP | 0 302 420 B1 | 7/1988 |
| EP | 0 707 186 A1 | 10/1995 |
| EP | 0 679 407 A2 | 11/1995 |
| EP | 0 799 621 A1 | 10/1997 |
| EP | 1 040 839 A1 | 10/2000 |

OTHER PUBLICATIONS

Penna, T.C.V., "The Presterilization Microbial Load On Used Medical Devices And The Effectiveness Of Hydrogen Peroxide Gas Plasma Against *Bacillus subtilis* Spores", Infection Control And Hospital Epidemiology, vol. 20(7), 465–72, Jul. 1999.

Morrissey, R.F., "Changes In The Science Of Sterilization And Disinfection", BI&T Forum, 30:404–06, Sep./Oct. 1996.

European Search Report, May 7, 2002.

* cited by examiner

*Primary Examiner*—Hoa Van Le
(74) *Attorney, Agent, or Firm*—Finnegan, Henderson, Farabow, Garrett and Dunner, L.L.P.

(57) ABSTRACT

The invention relates to a method for hydrogen peroxide plasma sterilization, wherein the chamber temperature is set at less than 39° C. throughout, and containers with temperature-sensitive products can be efficiently sterilized without the temperature-sensitive products showing a significant loss of activity or degradation.

25 Claims, 1 Drawing Sheet

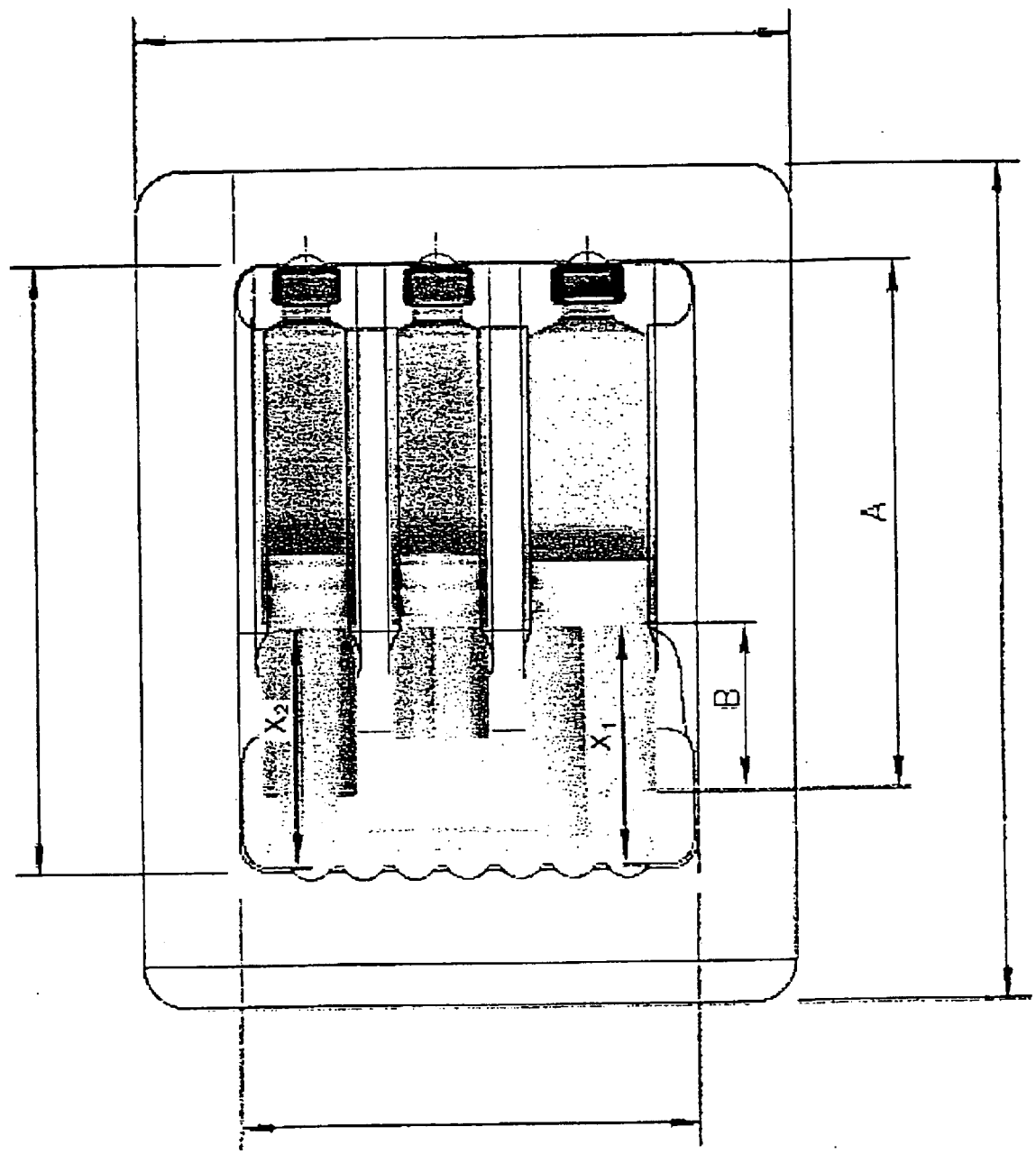

USE OF A HYDROGEN PEROXIDE PLASMA STERILIZATION METHOD FOR THE MILD STERILIZATION OF TEMPERATURE-SENSITIVE PRODUCTS

The invention relates to a method for hydrogen peroxide plasma sterilization, wherein the chamber temperature is set at less than 39° C. throughout, and containers with temperature-sensitive products can be efficiently sterilized without the temperature-sensitive products showing a significant loss of activity or degradation.

BACKGROUND OF THE INVENTION

The external sterilization of pharmaceutical containers which contain products which are sensitive to temperature effects or irradiation is a general problem which has not yet been satisfactorily solved.

Autoclaving is virtually always unsuitable for biological products because even the most stable products usually do not withstand this thermal stress.

Industrially used sterilization with ethylene oxide ordinarily requires temperatures of about 40–50° C., typically for a period totaling about 24–48 hours, inter alia, in order to remove the remaining ethylene oxide as completely as possible. However, these conditions are often unacceptable for temperature-sensitive products. An additional factor is that possible residual amounts of ethylene oxide or its reaction products in the packaging represent a disadvantage of this method because of its carcinogenicity and toxicity.

Another method, irradiation with γ rays or electron beams, is also usually unsuitable for sensitive products, especially in the liquid state, because it is associated, for example, with losses of activity and/or product degradation.

In the 1980s, a sterilization method which aimed at sterilization under reduced pressure (<1 torr) with hydrogen peroxide in the gas phase was described by EP-A 0 302 420. Although a description of this process at room temperature was also given, its sterilization efficiency is inadequate for a reliable method for routine use to be developed therefrom. The efficiency of this method is increased only by raising the temperature to at least 40° C.

In the sterilization method using hydrogen peroxide and generation of a gas plasma, chamber temperatures of 45° C. or 40–45° C. are also usual (T. C. V. Penna, C. A. M. Ferraz, and M. A. Cassola; Infection Control and Hospital Epidemiology 20: 465–472 (1999) and R. F. Morrissey; Biomedical Instrumentation & Technology 30: 404–406 (1996)). According to U.S. Pat. No. 4,643,876 or EP 207 417 in fact temperatures of 57° C. are measured in the material to be sterilized, because the method itself leads to warming of the sterilization material. Although this method has been described as low-temperature method or low-temperature plasma, the temperatures which are used or reached are still so high that sensitive products are at least partly damaged on exposure to this temperature.

The hydrogen peroxide plasma sterilization method has been employed, under the name STERRAD® method, since the early 1990s in Europe and the USA essentially for sterilizing medical instruments. Thus, the great majority of the corresponding applications are to be found in the hospital sector. There are, however, also a few applications, for example for products, appliances or disposable articles which can be employed in medicine, where the use of ethylene oxide or γ irradiation has been prohibited for compatibility reasons. These products can then often be sterilized without loss of functionality at the temperatures which are intrinsic to the hydrogen peroxide plasma sterilization method, a chamber temperature of about 45° C.

The STERRAD® method has to date been restricted to a chamber temperature of 45° C. (STERRAD® 100) or >39° C. (STERRAD® GMP 100) because it was necessary to assume on the basis of the known results (for example, EP-A 0 302 420) that effective sterilization can be achieved only at temperatures above 39° C. Our own tests with the hydrogen peroxide plasma sterilization method at the standard chamber temperature of 45° C. with biological products under the conditions which are assumed to be mild according to the prior art have shown that sensitive biological materials in some cases suffered marked or complete losses of activity (see example 1). It is thus impossible for the latter to be sterilized under the known conditions of the STERRAD® method.

DESCRIPTION OF THE INVENTION

The present invention was based on the object of developing a procedure which permits sensitive biological and therapeutic products to be sterilized externally in the solid or liquid state in their final container (primary packaging). It was moreover intended that the selection of the final container ensure that there is no adverse effect on the product by the method. It was additionally intended for it to be possible to sterilize the product in two outer packages (secondary packaging).

This object has been achieved in that it was possible to develop, on the example of the temperature-sensitive components of a fibrin glue, a modification of the hydrogen peroxide plasma sterilization method at a further reduced temperature which permits final containers with sensitive products, even in outer packages, to be efficiently sterilized externally in a rapid and mild manner.

BRIEF DESCRIPTION OF THE DRAWINGS

The scheme depicted shows cartridges as primary packaging materials, closed with seal and cap as well as a plunger stopper. In order to avoid plunger stopper movements during processes where also vacuum steps are applied, the cartridges and plunger stoppers are fixed with a spacer within the secondary packaging, e.g. a hard blister with Tyvek® lid. In addition to the first secondary packaging a further pouch manufactured of a gas permeable material may be used.

A: Cartridge length.

B: Distance between plunger stoper and cartridge end.

X1 and X2: Length of spacer for fixation of the plungers, adjusted in length to the distance between plunger and secondary packaging.

DETAILED DESCRIPTION OF THE INVENTION

It has now been found that containers with temperature-sensitive products can be effectively sterilized with hydrogen peroxide/plasma under modified conditions without the previously customary temperatures necessarily being used or occurring during this process. At chamber temperatures below 39° C. it is possible to achieve both product stability and sterility. At chamber temperatures of 20–39° C., especially also at about 25–35° C., very mild sterilizations of products are possible. It is thus possible through introduction of this low-temperature modification for final containers with sensitive products such as, for example, proteins, peptides, etc. in solution to be efficiently sterilized. Crucial for the low product temperature in this case is both the low chamber temperature and the avoidance of an excessive energy input, for example on injection of the hydrogen peroxide and in the plasma formation.

Before carrying out the sterilization, the products can, where appropriate, be exposed to a preplasma in order to remove moisture, as described in EP 707 186, or in order to further adapt the product temperature to the chamber temperature.

In the sterilization cycle to be applied, it is possible for the duration of the so-called injection period(s) and diffusion period(s) (where appropriate with simultaneous ventilation) to be varied, preferably between about 1 and 60 minutes. Ventilation during the diffusion period can, where appropriate, also be dispensed with, especially if the product to be sterilized has a simple geometry.

The injection of hydrogen peroxide solution can also be repeated one or more times—especially if the chamber is fully loaded—in order to achieve an adequate hydrogen peroxide content in the gas phase and thus an increased kill rate. If necessary, it is also possible for the entire cycle or parts thereof to be repeated one or more times, although the chamber temperature must be set at <39° C. in accordance with the claimed method in order to limit the warming.

If the diffusion period with ventilation is omitted, it is possible for the injection period, the restoration of an adequate vacuum and the plasma to be followed by a half cycle of injection, vacuum and plasma. This may with simple product geometries reduce the duration of the cycle.

This method makes it possible for the final containers of sensitive biological products such as, for example, proteins or peptides to be sterilized in short cycles at low temperature. As it has been possible to show in the case of blood plasma proteins, a mild sterilization of products in the final containers is possible with the method of the invention. Such products can then be employed wherever sterile handling is necessary.

However, it is also possible in principle to apply the described procedure to other sensitive biological products such as DNA, RNA, lipids, cellular products, etc. No significant losses are to be expected with said products owing to the short and low temperature stress.

The method of the invention can, however, also be employed generally for sterilizing final containers containing temperature-sensitive non-biological products. Possible examples thereof are synthetic compounds or products which can be employed in therapy but which, because of their temperature sensitivity, are partly or completely inactivated or damaged in conventional methods.

In the selection of the final container, i.e., the primary packaging, care must be taken that movable closures such as stoppers, plunger seals or caps are fixed so that no opening and no leak occurs in the primary packaging under vacuum. This can be prevented, for example, by appropriate devices, whether by directly fixing the closures or by ensuring by an appropriate secondary packaging that no leak or displacement of stoppers or plunger seals can occur (see FIG. 1).

A typical half cycle of the method of the invention at reduced temperature consists of the following elements:
Preparation (to be Carried Out if Required):

lowering the pressure in the treatment chamber, preferably to about 100 to 800 mtorr, very preferably to about 300 to 600 mtorr.

applying a preplasma, preferably for about 1 to 30 min, very preferably for about 2 to 15 min, ventilating, preferably in less than 5 min, very preferably in less than 1 min.

Procedure for a Half Cycle with a Chamber Temperature Set at <39° C. Preferably at About 20–35° C.:

lowering the pressure in the treatment chamber, preferably to about 100 to 800 mtorr, very preferably to about 300 to 600 mtorr.

introducing the hydrogen peroxide, usually by direct evaporation of a solution in vacuo one or more times, with subsequent distribution in the chamber (injection), preferably within 20 min, very preferably within 15 min, where appropriate additional hydrogen peroxide diffusion period (where appropriate with ventilation of the chamber), depending on the requirements for the product to be sterilized, preferably for 1 to 30 min, very preferably for 3 to 15 min, renewed lowering of the pressure and restoration of an adequate vacuum, generation of a plasma, preferably for 0.5 to 10 min, very preferably for 1 to 5 min, ventilation.

A complete sterilization cycle usually comprises two half cycles. This division has been made for reasons of method validation. If the reduction factor achieved in such a half cycle with model microorganisms such as, for example, spores of Bac. stearothermophilus is $\log_{10}$ CFU$\geq$6, the method can be said to be efficient with adequate certainty.

The method to which the invention relates is essentially described in the claims. Examples 2–6 show, on the basis of a modified sterilization method for primary packagings containing temperature-sensitive proteins such as, for example, the components of a fibrin glue, how effective sterilization is possible at low temperature without adversely affecting the properties of the protein components.

Example 1 shows the result of a hydrogen peroxide plasma sterilization run under standard temperature conditions according to the prior art. The following examples (2–6) are intended to illustrate the principle of the modified method at low temperature.

COMPARATIVE EXAMPLE 1

Various protein solutions (main constituent of protein solution 1: fibrinogen, of protein solution 2: factor XIII and of protein solution 3: thrombin) were dispensed into glass carpules and sealed into bags consisting of Tyvek sheet and a transparent plastic sheet. The bags were then put in layers into baskets and treated in a STERRAD® GMP 100 sterilizer (supplier: Johnson & Johnson Medical GmbH, 22844 Norderstedt, Germany) with a hydrogen peroxide plasma sterilization method in accordance with the following parameters. The exact composition of the protein solutions used for carrying out the examples is immaterial. The solutions are ones known per se to the skilled worker and comprise biological proteins of natural or recombinant origin employed in therapy.

Preparation:

Chamber temperature set at 45° C. Loading of the chamber: basket charged with product-containing primary packagings in bags.

Procedure for the 1st Half Cycle:

| | |
|---|---|
| Vacuum: | to about 400 mtorr |
| Injection: | about 6 min (1 800 µl of 59% $H_2O_2$) |
| Diffusion: | 10 min (including ventilation) |
| Vacuum: | to about 400–500 mtorr |
| Plasma: | 2 min |

A 2nd, 3rd and 4th half cycle (corresponding to the 1st half cycle) are carried out directly following half cycle 1.

Results of the sterilization runs in example 1: stability of the investigated protein solutions:

|  | Content (% of initial levels) | | |
| --- | --- | --- | --- |
| Stage | Protein solution 1: Fibrinogen | Protein solution 2: Factor XIII | Protein solution 3: Thrombin |
| Content before sterilization | 100 | 100 | 100 |
| Content after 4 half cycles | Gel formulations; material unusable | 100 | 26.0 (turbidity) |
| Untreated control | 100 | 100 | 100 |

As is evident from the table for example 1, a temperature-dependent aggregation or degradation or denaturation occurs in the case of protein solution 1 (containing fibrinogen) and protein solution 3 (containing thrombin). This means that both products have become unusable for the intended application through the hydrogen peroxide plasma sterilization method according to the prior art.

EXAMPLE 2

Various protein solutions (main constituent of protein solution 1: fibrinogen, of protein solution 2: factor XIII and of protein solution 3: thrombin) were dispensed into glass carpules and sealed into bags consisting of Tyvek sheet and a transparent plastic sheet. The bags were then put in layers into baskets and treated in a STERRAD® GMP 100 sterilizer with a hydrogen peroxide plasma sterilization method in accordance with the following parameters.

Preparation:

Chamber temperature set at: 30° C.
Loading of the chamber: lower basket tightly packed with the described bags containing water-filled primary packaging; upper basket charged with product-containing bags and, in addition, a temperature sensor.

Loading Followed by Carrying Out a "Preplasma":

| Vacuum: | to about 400 mtorr |
| --- | --- |
| Preplasma: | 5 min |
| Ventilation | (brief) |

Procedure for a 1st Half Cycle:

| Vacuum: | to about 400 mtorr |
| --- | --- |
| Injection: | about 12 min (1 800 µl of 59% $H_2O_2$) |
| Diffusion: | 5 min (including ventilation) |
| Vacuum: | to about 400–500 mtorr |
| Plasma: | about 2 min |

Vacuum (brief) and ventilation (to remove sample)
A 2nd half cycle (corresponding to the 1st half cycle) is carried out directly following half cycle 1.

Results of the sterilization runs in example 2: stability of the investigated protein solutions:

|  | Content (% of initial levels) | | |
| --- | --- | --- | --- |
| Stage | Protein solution 1: Fibrinogen | Protein solution 2: Factor XIII | Protein solution 3: Thrombin |
| Content before sterilization | 100 | 100 | 100 |
| Content after 1st half cycles | 107.7 | 101.4 | 98.5 |
| Content after 2 half cycles | 104.3 | 100.5 | 98.2 |
| Untreated control | 100.9 | 99.5 | 98.6 |

EXAMPLE 3

Various protein solutions (main constituent of protein solution 1: fibrinogen, of protein solution 2: factor XIII and of protein solution 3: thrombin) were dispensed into glass carpules and sealed into bags consisting of Tyvek sheet and a transparent plastic sheet. The bags were then put in layers into baskets and treated in a STERRAD® GMP 100 sterilizer with a hydrogen peroxide plasma sterilization method in accordance with the following parameters.

Preparation:

Chamber temperature set at: 30° C.
Loading of the chamber: lower basket tightly packed with the described bags containing water-filled primary packaging; upper basket charged with product-containing bags and, in addition, a temperature sensor.

Loading Followed by Carrying Out a "Preplasma":

| Vacuum: | to about 400–500 mtorr |
| --- | --- |
| Preplasma: | 5 min |
| Ventilation: | (brief) |

Procedure for a 1st Half Cycle:

| Vacuum: | to about 400 mtorr |
| --- | --- |
| Injection: | about 17 min (1 800 µl of 59% $H_2O_2$) |
| Vacuum: | to about 400–500 mtorr |
| Plasma: | 2 min |

Vacuum (brief) and ventilation (to remove sample)
A 2nd half cycle (corresponding to the 1st half cycle) is carried out directly following half cycle 1.

Results of the sterilization runs in example 3: stability of the investigated protein solutions:

|  | Content (% of initial levels) | | |
| --- | --- | --- | --- |
| Stage | Protein solution 1: Fibrinogen | Protein solution 2: Factor XIII | Protein solution 3: Thrombin |
| Content before sterilization | 100 | 100 | 100 |
| Content after 1st half cycles | 101.7 | 101.9 | 98.9 |

-continued

| Stage | Content (% of initial levels) | | |
|---|---|---|---|
| | Protein solution 1: Fibrinogen | Protein solution 2: Factor XIII | Protein solution 3: Thrombin |
| Content after 2 half cycles | 101.2 | 101.9 | 98.6 |
| Untreated control | 100.9 | 99.5 | 98.6 |

EXAMPLE 4

Various protein solutions (main constituent of protein solution 1: fibrinogen, of protein solution 2: factor XIII and of protein solution 3: thrombin) were dispensed into glass carpules and sealed into bags consisting of Tyvek sheet and a transparent plastic sheet. The bags were then put in layers into baskets and treated in a STERRAD® GMP 100 sterilizer with a hydrogen peroxide plasma sterilization method in accordance with the following parameters.

In addition to product-filled primary packagings, in order to check the efficiency of sterilization carpules and strips with spores of a test organism (*Bac. stearothermophilus*) were sealed doubly in Tyvek bags.

Preparation:
Chamber temperature set at: 35° C.
Loading of the chamber: lower basket tightly packed with the described bags containing water-filled primary packaging; upper basket charged with product-containing bags, bags containing spore strips and primary packaging, and additionally a temperature sensor.
After loading a "preplasma" is carried out:

| | |
|---|---|
| Vacuum: | to about 400–500 mtorr |
| Preplasma: | 5 min |
| Ventilation | (brief) |

Procedure for a 1st Half Cycle:

| | |
|---|---|
| Vacuum: | to about 400 mtorr |
| Injection: | about 12 min (1 800 µl of 59% H2O2) |
| Diffusion: | 5 min (including ventilation) |
| Vacuum: | to about 400–500 mtorr |
| Plasma: | 2 min |

Vacuum (brief) and ventilation (to remove sample)
A 2nd half cycle (corresponding to the 1st half cycle) is carried out directly after half cycle 1.
Results of the sterilization runs in example 4: stability of the investigated protein solutions:

| Stage | Content (% of initial levels) | | |
|---|---|---|---|
| | Protein solution 1: Fibrinogen | Protein solution 2: Factor XIII | Protein solution 3: Thrombin |
| Content before sterilization | 100 | 100 | 100 |
| Content after 1st half cycles | 106.9 | 108.0 | 99.3 |
| Content after 2 half cycles | 102.7 | 104.7 | 99.6 |
| Untreated control | 100.9 | 99.5 | 98.6 |

Sterility assessment of 8 spore strips treated in a half cycle:

| | Sterility assessment of the employed spore strips No. | | | | | | | |
|---|---|---|---|---|---|---|---|---|
| | 1 | 2 | 3 | 4 | 5 | 6 | 7 | 8 |
| Number of spores per spore strip before the half cycle (× $10^6$) | 2.2 | 2.2 | 2.2 | 2.2 | 2.2 | 2.2 | 2.2 | 2.2 |
| Content after 1st half cycles | 0 | 0 | 0 | 0 | 0 | 0 | 0 | 0 |

EXAMPLE 5

Various protein solutions (main constituent of protein solution 1: fibrinogen, of protein solution 2: factor XIII and of protein solution 3: thrombin) were dispensed into glass carpules and sealed into bags consisting of Tyvek sheet and a transparent plastic sheet. The bags were then put in layers into baskets and treated in a STERRAD® GMP 100 sterilizer with a hydrogen peroxide plasma sterilization method in accordance with the following parameters.

Preparation:
Chamber temperature set at: 35° C.
Loading of the chamber: lower basket tightly packed with the described bags containing water-filled primary packaging; upper basket charged with product-containing bags and, in addition, a temperature sensor.
Loading Followed by Carrying Out a "Preplasma":

| | |
|---|---|
| Vacuum: | to about 400–500 mtorr |
| Preplasma: | 5 min |
| Ventilation | (brief) |

Procedure for a 1st Half Cycle:

| | |
|---|---|
| Vacuum: | to about 400 mtorr |
| 1st injection: | about 2 min (1 800 µl of 59% $H_2O_2$) |
| 2nd injection: | about 10 min (1 800 µl of 59% $H_2O_2$) |
| Diffusion: | 5 min (including ventilation) |
| Vacuum: | to about 400–500 mtorr |
| Plasma: | 2 min |

Vacuum (brief) and start with next half cycle or ventilation (to remove sample)
A 2nd, 3rd and 4th half cycle (corresponding to the 1st half cycle) are carried out directly following half cycle 1.

Results of the sterilization runs in example 5: stability of the investigated protein solutions:

| | Content (% of initial levels) | | |
|---|---|---|---|
| Stage | Protein solution 1: Fibrinogen | Protein solution 2: Factor XIII | Protein solution 3: Thrombin |
| Content before sterilization | 100 | 100 | 100 |
| Content after 2 half cycles | 94.5 | 102.9 | 100.3 |
| Content after 4 half cycles | 92.0 | 108.1 | 100.3 |
| Untreated control | 97.5 | 106.2 | 99.3 |

EXAMPLE 6

To test the sterilization efficiency of the method in a maximally loaded chamber with commercial packaging materials, water-filled glass carpules were sealed into outer packages consisting of PET hard blisters, closed with Tyvek paper, and additionally with bags consisting of Tvvek paper and a transparent plastic sheet. The packages were than put in tight layers into baskets and treated in a STERRAD® GMP 100 sterilizer with a hydrogen peroxide plasma sterilization method according to the following parameters.

Strips of spores of a test organism (*Bac. stearothermophilus*) were introduced into the double packaging and sealed in the least accessible positions of eight blister packs distributed at different positions in the baskets in order to check the sterilization efficiency.

Preparation:
Chamber temperature set at: 32° C.
Loading of the chamber: lower and upper basket tightly packed with the described packages (172 items) containing water-filled primary packaging; 8 packages contained in addition to the primary packagings also spore strips (between carpule and hard blister or between carpule end and stopper retainer) and were distributed in accordance with a defined plan in the baskets.
Procedure for a "Preplasma":

| | |
|---|---|
| Vacuum: | to about 400–500 mtorr |
| Preplasma: | 5 min |

Procedure for a Half Cycle:

| | |
|---|---|
| Vacuum: | to about 400–500 mtorr |
| 3 injections: | lasting about 3, 6 and 6 min respectively (each of 1 800 µl of 59% $H_2O_2$) |
| Diffusion: | 5 min (including ventilation) |
| Vacuum: | to about 400–500 mtorr |
| Plasma: | 2 min |

Vacuum (brief) and ventilation (to remove sample)

Results of the sterilization run in example 6: sterility assessment of 8 spore strips treated in a half cycle:

All of the spore strips employed were completely inactivated, even those in the least accessible positions, i.e., this method made it possible to sterilize more than 106 spores effectively in one half cycle.

| | Sterility assessment of the employed spore strips No. | | | | | | | |
|---|---|---|---|---|---|---|---|---|
| | 1 | 2 | 3 | 4 | 5 | 6 | 7 | 8 |
| Number of spores per spore strip before the half cycle ($\times 10^6$) | 2.6 | 2.6 | 2.6 | 2.6 | 2.6 | 2.6 | 2.6 | 2.6 |
| Spores detectable after a half cycle | 0 | 0 | 0 | 0 | 0 | 0 | 0 | 0 |

What is claimed is:

1. A process for hydrogen peroxide plasma sterilization comprising:
    (a) inserting at least one primary container containing a temperature-sensitive material into a sterilization treatment chamber;
    (b) lowering the pressure in the treatment chamber to create a vacuum;
    (c) injecting, at least one time, hydrogen peroxide into the chamber;
    (d) lowering the pressure in the treatment chamber to reestablish a vacuum;
    (e) generating a plasma; and
    (f) ventilating the chamber;
    wherein the chamber temperature is less than 39° C. throughout the process, the temperature-sensitive material is sterilized and stable, and wherein the pressure in step (d) is about 100 to 800 mtorr.
2. The process of claim 1, wherein the pressure in step (b) is about 100 to 800 mtorr.
3. The process of claim 1, wherein step (c) is performed from between 1 and 60 minutes.
4. The process of claim 1, wherein prior to step (d) a hydrogen peroxide diffusion step is performed simultaneously with ventilation.
5. The process of claim 1, wherein prior to step (d) a hydrogen peroxide diffusion step is performed without ventilation.
6. The process of claim 4, wherein the hydrogen peroxide diffusion step is performed from between 1 and 60 minutes.
7. The process of claim 5, wherein the hydrogen peroxide diffusion step is performed from between 1 and 60 minutes.
8. The process of claim 1, wherein the temperature of the temperature-sensitive material does not rise above 40° C. during the sterilization process.
9. The process of claim 1, wherein the temperature-sensitive material comprises biological materials.
10. The process of claim 9, wherein the biological materials are proteins, peptides, nucleic acids, lipids, or cellular materials.
11. The process of claim 9, wherein the biological material is a fibrogen containing solution.
12. The process of claim 9, wherein the biological material is a Factor XIII containing solution.
13. The process of claim 9, wherein the biological material is a thrombin containing solution.
14. The process of claim 9, wherein the biological material comprises the components of tissue glue.
15. The process of claim 9, wherein the biological material comprises the components of fibrin glue.
16. The process of claim 1, wherein the temperature-sensitive material comprises non-biological materials.
17. The process of claim 1, wherein the process is performed more than one time.

18. The process of claim 1, wherein before step (b), a preplasma step is performed comprising:

lowering the pressure in the treatment chamber to create a vacuum;

applying a preplasma; and ventilating the chamber.

19. The process of claim 18, wherein the pressure is about 100 to 800 mtorr.

20. The process of claim 18, wherein the preplasma is applied for about 1 to 30 minutes.

21. The process of claim 18, wherein the ventilation step is no greater than 5 minutes.

22. The process of claim 1, wherein the primary container is enveloped at least one time with materials partially permeable to hydrogen peroxide.

23. The process of claim 1, wherein the primary container containing the temperature-sensitive material is placed in a secondary container.

24. The process of claim 1, wherein the chamber temperature is between 20–39° C.

25. The process of claim 24, wherein the chamber temperature is between 25–35° C.

* * * * *